United States Patent

Dementhon et al.

[11] Patent Number: 6,107,603
[45] Date of Patent: Aug. 22, 2000

[54] DEVICE INTENDED TO DETECT FOULING AND TO LOCALLY HEAT AN ELECTRICAL INSULATING MEDIUM

[75] Inventors: Jean-Baptiste Dementhon, Paris; Brigitte Martin, Saint Genis Laval, both of France

[73] Assignee: Institut Francais du Petrole, Cedex, France

[21] Appl. No.: 09/035,847

[22] Filed: Mar. 6, 1998

[30] Foreign Application Priority Data

Mar. 7, 1997 [FR] France .................................. 97 02823

[51] Int. Cl.[7] ........................................................ B60L 1/02
[52] U.S. Cl. .................................. 219/202; 55/288; 55/301
[58] Field of Search .............................. 55/288, 301, 312, 55/38.5, DIG. 30, 267, 284, DIG. 10, 212, 213, 270, 274; 60/288, 311, 303; 123/198 E; 219/202; 392/485, 487, 488, 489, 490

[56] References Cited

U.S. PATENT DOCUMENTS 4,829,766  5/1989  Henkel .
4,872,889  10/1989  Lepperhoff et al. ....................... 55/267
5,171,337  12/1992  Pollock ..................................... 55/284
5,551,971  9/1996  Chadderton et al. ....................... 95/15
5,595,580  1/1997  Kawamura ............................... 55/288

FOREIGN PATENT DOCUMENTS 0525566  2/1993  European Pat. Off. .
0682174  11/1995  European Pat. Off. .
WO 9308382  4/1993  WIPO .

OTHER PUBLICATIONS

Search Report.

*Primary Examiner*—Teresa Walberg
*Assistant Examiner*—Leonid Fastovsky
*Attorney, Agent, or Firm*—Anotnelli, Terry, Stout & Kraus, LLP

[57] ABSTRACT

A device intended to measure fouling and to locally heat an electrical insulating medium. At least one electrically resistive heating element (6, 8) is associated with a fouling detection unit. The fouling detection unit includes metallic elements (6, 10) in contact, at at least two points, with the insulating medium. The resistance variation between the two points is measured and is directly linked with the fouling of the medium.

16 Claims, 2 Drawing Sheets

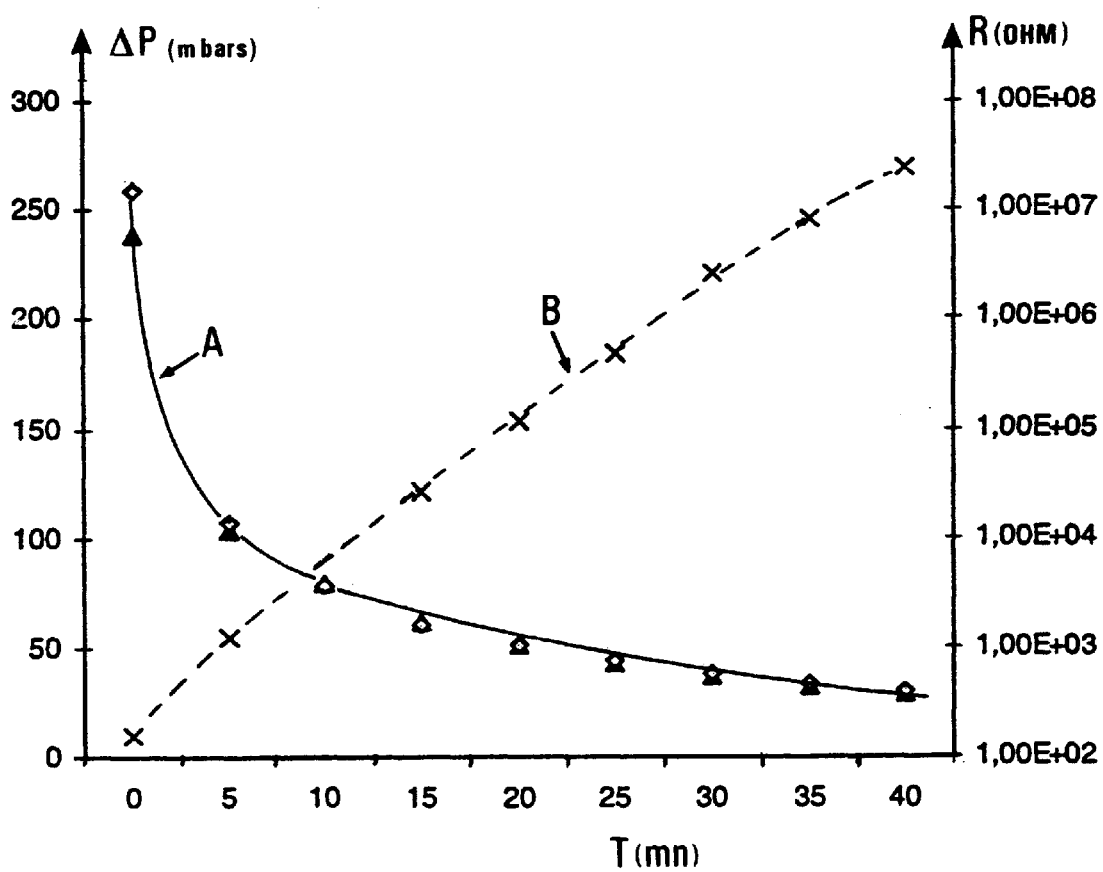

DEVICE INTENDED TO DETECT FOULING AND TO LOCALLY HEAT AN ELECTRICAL INSULATING MEDIUM

The present invention relates to a device intended to measure fouling and to locally heat an insulating medium, comprising at least one heating resistive element (6, 8) associated with a fouling detection means.

More precisely, said fouling detection means comprises metallic elements (6, 10) in contact, at at least two points, with the insulating medium, between which the resistance variation is measured, said resistance being directly linked with the fouling of said medium.

FIELD OF THE INVENTION

The present invention relates to the field of measurement and management of the local fouling of an electrical insulating medium, and notably of an insulating filtering medium.

The fouling considered consists, for example, of a soot or particle deposit exhibiting an electrical conductivity.

The present invention also relates to the measurement of the proportion of particles contained in a gas via measurement of the fouling of a "test" insulating medium placed in the gas flow.

The aim of the invention is also to be able to measure the fouling of electrical insulating mediums that become progressively covered with an electrically conducting deposit and to initiate a "cleaning" process.

Among the preferred embodiments of the invention, a heating fouling detector capable of regenerating a particulate filter placed in the exhaust line of an internal-combustion engine, and more particularly of a diesel engine, can be mentioned.

BACKGROUND OF THE INVENTION

In fact, since diesel engines generate particularly high proportions of particles, providing exhaust lines with particulate filtering means can be considered. These means hold the particles back with high filtering efficiencies of the order of 80%. The ceramic monolith marketed by the Corning Company or the cartridge with coiled ceramic fibers, such as that described in Patent Cooperation Treaty patent application WO-95/27,843 can be mentioned by way of examples.

The technical difficulty encountered in the development of particulate filters is that they have to be periodically regenerated by combustion of the soot deposit. This combustion sometimes occurs naturally when the temperature of the gases reaches by itself the level required to initiate oxidation of the particles. However, average operating conditions generally lead to temperatures that are too low to spontaneously initiate combustion of the particles. This then leads to clogging of the filter, which is detrimental to the engine efficiency and eventually threatens the running thereof. The filter then has to be regenerated artificially.

Many techniques have been developed to that end. These techniques can be based on changes in the running of the engine intake throttling, exhaust throttling, advanced injection lag, or the techniques can be linked with energy supply in the exhaust gases or at the level of the filter (resistor, burner, micro-wave, . . . ). It is then necessary to control these various devices by means of an outer control driven by a computer. Most often, the criterion taken into account for regeneration initiation is the back pressure in the exhaust line.

In order to facilitate regeneration of particulate filters, a different approach of chemical nature consists in adding to the fuel an additive, for example an organometallic additive, that is thereafter found on the soot deposit, which generally leads to a decrease in the ignition temperature and therefore to a regeneration frequency increase.

Examples of the products most commonly used as additives are copper, iron, cerium, and sodium. Studies show that, in the presence of such additives, partial regenerations can occur spontaneously at relatively low exhaust gas temperatures (in the order of 200° C.).

However, for certain driving modes, problems linked with the back pressure can subsist, so that an external power supply such as electric heating can be necessary.

Concerning power consumption, most of the well-known systems using electric heating perform a global heating of the filtering element. This leads to a high power consumption that is more or less controlled. Generally, the electrical power required to initiate total regeneration of the filter is high and often hardly compatible with the electrical resources on board the vehicle. European Patent EP-B1-0, 485,179 illustrates a system based on this principle.

Besides, the regeneration conditions can greatly depend on the fouling condition of the filter.

French patent application EN.96/13,855 filed in the name of the applicant brings a solution to the problem of energy consumption of a regeneratable filtering set, whatever the running conditions of an engine.

According to this document, a filtering element is locally heated as a function of a global fouling measurement.

According to French patent application EN.96/11,292, the geometry of a filtering means is adapted as a function of predetermined strategies linked with the running of the engine.

In the field of fouling measurement in particulate filters, fouling detectors whose only purpose is to determine the degree of fouling of the filters are well-known.

The present invention overcome the aforementioned drawbacks and goes beyond the fouling measurement proper.

SUMMARY OF THE INVENTION

The object of the present invention is thus a device intended to measure locally the fouling of an electrical insulating medium and to heat it locally.

According to the invention, the device comprises at least one heating resistive element associated with a fouling measuring means.

More precisely, the device according to the invention can comprise several heating resistive elements used as fouling detection means.

In particular, said fouling detection means comprises metallic elements arranged at at least two points of the insulating medium, between which metallic elements the resistance variation is measured, the resistance being directly linked with the fouling of the medium.

According to an embodiment of the invention, the device comprises at least one coil placed at one point of the electrical insulating medium, the coil comprising a metallic central core covered with an insulating material that is itself covered with a metallic sheath.

More particularly, the device according to the invention can further comprise an insulating zone interposed over a length of the resistive element, a conducting sheath placed around the resistive element, and several electrodes associated with the conducting sheath and placed on either side of said insulating zone.

Furthermore, the device according to the invention can comprise a means intended to start the power supply of at least one of the resistive elements as a function of the resistance measurement linked with the fouling of the electrical insulating medium.

The means thus receives the resistance value(s) and reacts by activating at least one heating resistive element.

The means can be an electronic computer which allows to adapt in an optimum way the number of resistors activated as a function of the measurement of the fouling detected and/or of the energy resources available.

The device according to the invention can be used in a filtering medium in order to regenerate it locally.

Without departing from the scope of the invention, the device can be used in an exhaust line of an internal-combustion engine in order to detect the proportion of particles contained in the exhaust gases.

The device according to the invention can be advantageously used in a filtering means placed in the exhaust line of an internal-combustion engine.

BRIEF DESCRIPTION OF THE DRAWINGS

Other features, details and advantages of the present invention will be clear from reading the description hereafter, given by way of non limitative example, with reference to the accompanying drawings wherein.

DETAILED DESCRIPTION OF THE INVENTION

Figure 1:
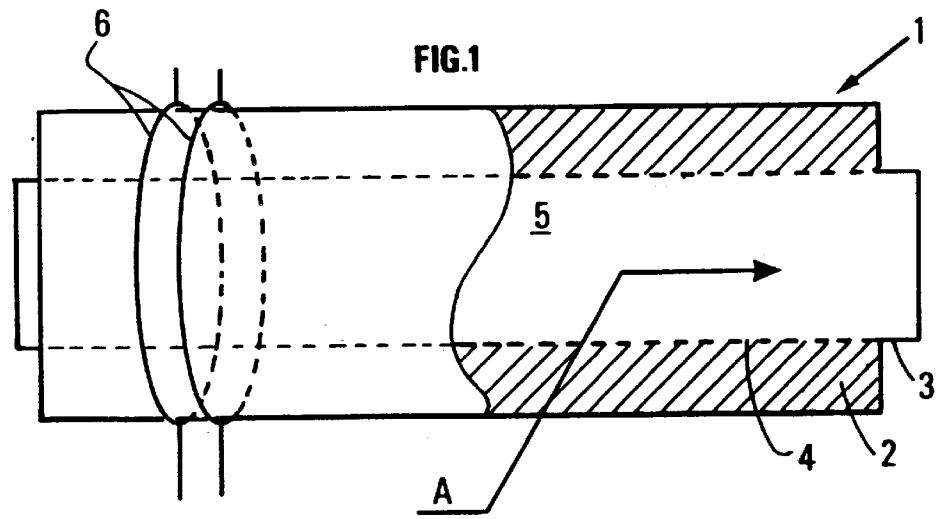
FIG. 1 is a simplified longitudinal section of an electrical insulating filtering medium.

FIG. 1 is a longitudinal section of a filter cartridge 1 known in the art, equipped with a fouling measuring device.

The cartridge shown here has the shape of a cylinder whose thickness consists of a medium 2 which is both filtering and electrically insulating. Medium 2 is supported in the central part thereof by a metallic rigid tube 3. Tube 3 is pierced with an array of ports 4 allowing passage of the gases.

The gases flow in the direction shown by arrow A in FIG. 1, i.e. they flow in from the outside of the cartridge, flow radially through filtering medium 2, then through the ports 4 of tube 3 and eventually reach the central zone 5 of cartridge 1.

At least one heating resistive element 6 can be placed on such a cartridge.

According to FIG. 1, two heating resistive elements 6 are wound around two specific zones of the cartridge.

Elements 6 are supplied separately and connected separately to an ohmmeter in order to measure the resistance between them. In the absence of fouling of filtering medium 2, the electrical resistance will be infinite since the medium 2 is insulating. As fouling progresses, i.e. as the accumulation of particles between the electrodes increases, contact is made and the resistance progressively decreases, thus allowing one to follow the evolution of the fouling between the two elements 6.

Elements 6 can consist, as it is well-known in the art, of a metallic core which allows heat release by resistance heating when switched on. This core is covered with an insulating material that is itself contained in an external metallic sheath.

This metallic sheath is used here as an electrode of the resistance detector.

A single element 6 such as that described can be wound around cartridge 1, and a simple metallic electrode for example connected to metallic tube 3 can form the second electrode of the fouling detector.

Figure 2:
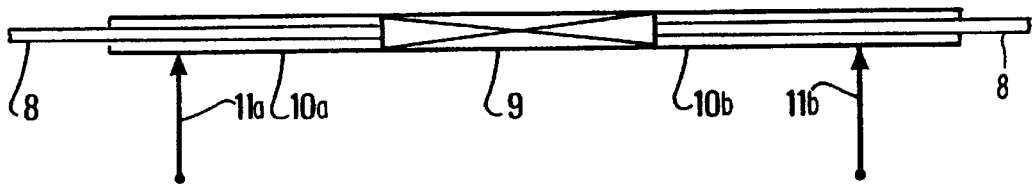
FIG. 2 is a flowsheet of an embodiment of the invention.

FIG. 2 relates to an embodiment of the invention. This device comprises a threadlike metallic core 8 which forms a heating resistive element. An insulating zone 9 is interposed over a certain length of metallic core 8. External conducting sheaths 10a, 10b also cover metallic core 8. Electrodes 11a, 11b are arranged on conducting sheaths 10a, 10b respectively at a certain distance from one another, on either side of insulating zone 9.

This device can be brought into contact with the electrical insulating medium to be controlled, such as the filter cartridge 1 mentioned above. It can be noted that implementation of the invention does not require the medium to be filtering.

Thus, in the absence of fouling, the resistance between the two terminals 11 is infinite in view of the presence of insulating zone 9.

When a deposit of particles exhibiting a certain conductivity forms on the medium to be controlled, the resistance measured at terminals 11 decreases. The measurement principle mentioned in connection with FIG. 1 applies similarly here.

A given resistance threshold can be utilized to set off the supply of heating element 8 in order to regenerate the fouled medium.

Of course, other resistance measurements can be performed if other elements 6 and/or electrodes are placed on a cartridge.

The resistive elements 6, 8 according to the invention allow local heating of a precise zone of a cartridge, which is very interesting as regards the energy required for regeneration of the cartridge.

Figure 3:
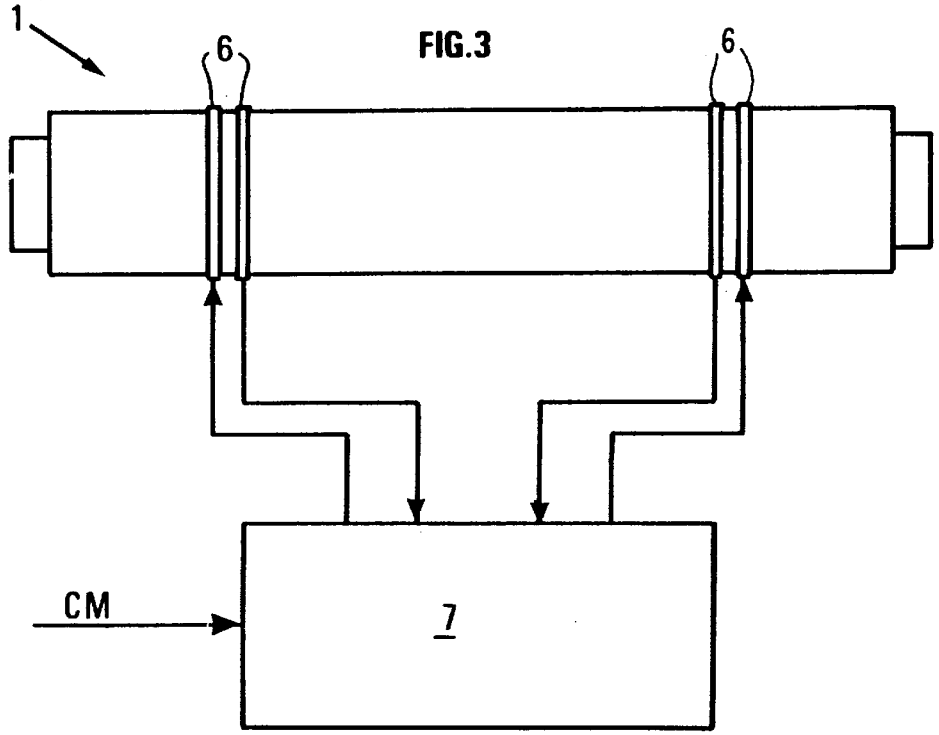
FIG. 3 is an overall view of an embodiment of the invention, FIG. 4 graphically relates measurements showing the correlation with time of the back pressure values and the resistance values.

Furthermore, as shown in FIG. 3, illustratively with respect to the embodiment of FIG. 1, a computer 7, or any other means fulfilling the same purpose is connected to resistive elements 6, 8. Computer 7 to activate selectively the resistive elements as a function of the information linked with the local fouling. A computer 7 can similarly be utilized with the embodiment of FIG. 2. It is thus possible to assign a fouling threshold to each resistance measured locally, a threshold which activates at least one resistive element 6, 8, and therefore the regeneration of a zone of cartridge 1.

The maximum fouling, locally assessed, can be characterized by a threshold resistance level. Below this value, a heating element corresponding to a considered zone is switched on. The electrical power required to heat such an element to the soot combustion temperature is very low on account of the location of the heating resistor. It is thus possible to adopt a strategy of heating of the other elements so as to propagate the combustion initiated locally.

Heating can also for example be restricted to the zones which remain fouled after a regeneration (incomplete regeneration). These strategies only constitute possible examples. The general principle consists in adapting the number of resistors supplied as a function of the fouling condition of the filter, identified from the local resistance of the particle deposit and from the running conditions of the engine.

According to the invention, computer 7 receives at least one resistance measurement and reacts by activating or not an associated resistive element or any other resistive element capable of heating locally the insulating medium.

Various strategies can be stored in computer 7, which can also take into account other parameters linked for example, with the running conditions of the engine, inputted as shown by arrow CM in FIG. 3.

As shown in FIG. 4, the measured values of the resistance (R) and of the back pressure ($\Delta P$) at the exhaust evolve in opposite ways with time: respectively curve A and curve B.

Knowing that the back pressure ($\Delta P$) is a value indicative of the fouling condition of the filtering insulating medium, it can be seen that the measurement of the resistance (R) according to the invention, which varies inversely in relation to the back pressure ($\Delta P$), is therefore just as indicative of the fouling condition.

Conventionally, the back pressure at the exhaust ($\Delta P$) (curve B) increases with time as the medium fouls up.

FIG. 4 shows that the resistance (R) according to the invention (curve A) decreases greatly during the first ten minutes of use. The decrease is lower thereafter.

Processing of the resistance values, as mentioned above by way of example, can thus allow one to manage the fouling very precisely, both in time and in space. An energy saving obviously and advantageously results therefrom. Besides, the thermal stresses are better controlled, which improves the life of the system.

Without departing from the scope of the present invention, the resistive elements 6 according to FIG. 1 can be installed on an electrical insulating medium placed in a gas stream. Measurement of the evolution with time of the fouling of the electrical insulating medium according to the invention thus provides information about the average proportion of particles over the considered period in the gas flow. Such equipment could, for example, be used to control the emissions discharged by a vehicle, according to a standard driving cycle, in vehicle control centers.

The embodiment of the invention according to FIG. 2 allows the same use with a very simple implementation, since a device such as that shown in FIG. 2 is to be placed in the gas stream. The variation with time of the particle deposit thus allows one to detect the evolution of the proportion of particles in the gas stream.

This embodiment of the invention can also be used to detect the fouling of various mediums such as turbine elements, and industrial chimneys. A device according to FIG. 2 is then placed on the medium to be controlled is connected to a control means such as an electronic computer 7.

Furthermore, the present invention can be used in one or the other filtering sets described in French applications EN.96/11,292 or EN.96/13,855 filed in the name of the applicant.

What is claimed is:

1. A device for measuring fouling of and for heating an elongated electrical insulating medium, said device comprising an elongated electrically resistive heating element, an elongated electrically conductive sheath, having an insulating zone intermediate the ends thereof, arranged around said resistive heating element and adapted to contact the electrical insulating medium; and a plurality of spaced apart electrodes contacting said conductive sheath at longitudinally spaced locations on either side of said insulating zone.

2. A device as claimed in claim 1, further comprising means for applying power from an electrical power supply to said electrodes in response to measurement of an electrical resistance value indicating fouling of the insulating medium.

3. A device as claimed in claim 2, wherein said means comprises an electronic computer.

4. A device as claimed in claim 3, where said computer applies the power to a number of said electrodes, with the number being determined as a function of the level of the electrical resistance measured as a measurement of the fouling of the insulating medium.

5. A method of regenerating an elongated electrically insulating filtering medium, comprising contacting a longitudinally extending length of the filtering medium with an elongated electrically resistive heating element having an elongated electrically conductive sheath therearound, with an electrically insulating zone intermediate the ends of the sheath to define first and second heating element zones on the sheath on either side of the insulating zone; contacting the conductive sheath in the first and second heating element zones with first and second electrodes, respectively; measuring the electrical resistance between the first and second electrodes; and when the measured resistance indicates that the filtering medium is fouled to a preselected amount, applying electrical power to the first and second electrodes to cause electrically resistive heating of the heating element in order to initiate combustion of the fouling and regenerate the filtering medium.

6. A method of detecting the proportion of particles contained in exhaust gases in an exhaust line of an internal combustion engine, comprising inserting into the exhaust line an elongated electrically resistive heating element having an elongated electrically conductive sheath therearound, with an electrically insulating zone intermediate the ends of the sheath, and having an electrode contacting the sheath on either side of the insulating zone; and measuring the electrical resistance between the electrodes to provide an indication of the proportion of particles contained in the exhaust gases.

7. A method of treating a filtering medium in an exhaust line of an internal-combustion engine, comprising inserting into the exhaust line an elongated electrically resistive heating element having an elongated electrically conductive sheath therearound, with an electrically insulating zone intermediate the ends of the sheath, and having an electrode contacting the sheath on either side of the insulating zone; measuring the electrical resistance between the electrodes to provide an indication of the condition of the filtering medium; and when the measured resistance indicates a preselected condition, applying electrical power to the electrodes to cause electrically resistive heating of the heating element in order to initiate combustion of the fouling and regenerate the filtering medium.

8. A device for measuring fouling and for locally heating an elongated electrical insulating medium, said device comprising first and second electrically resistive heating elements formed as conductive loops adapted to be wrapped around the electrical insulating medium, so as to have a portion of the electrical insulating medium providing an insulating zone in a gap between the heating elements; and first and second electrodes contacting said first and second heating elements, respectively, on either side of the insulating zone.

9. A method of treating an elongated electrical insulating medium, comprising looping first and second electrically resistive heating elements about the insulating medium at first and second locations having a portion of the insulating medium therebetween to provide a gap between the heating elements; measuring the electrical resistance between the heating elements to provide an indication of the condition of the insulating medium; and when the measured resistance indicates a preselected condition, applying electrical power to the resistive heating elements to resistively heat the heating elements and regenerate the insulating medium.

10. A device for regenerating an elongated electrically insulating filtering medium, comprising an elongated electrically resistive heating element; an elongated electrically conductive sheath, having an insulating zone intermediate the ends thereof, arranged around the resistive heating element, the insulating zone defining first and second longitudinally spaced heating element zones on either side of the insulating zone; first and second electrodes contacting the elongated electrically conductive sheath in the first and second heating element zones, respectively; means for measuring the electrical resistance between the first and second electrodes; and means responsive to the measured electrical resistance being less than a pre-determined valve for applying electrical power to the first and second electrodes to cause electrically resistive heating of the heating element in order to initiate combustion of the fouling and regenerate the filtering medium.

11. A device for measuring fouling of and for heating an elongated electrical insulating medium, said device comprising:

an elongated electrically resistive heating element;

an elongated electrically conductive sheath, having an electrically insulating zone intermediate the ends thereof, arranged around the resistive heating element, said insulating zone dividing said electrically conductive sheath into first and second electrically resistive heating zones;

first and second electrodes contacting said electrically conductive sheath in the first and second electrically resistive heating zones at first and second longitudinally spaced points;

means for measuring the electrical resistance between said first and second electrodes to obtain an indication of fouling of the electrical insulating medium between the first and second longitudinally spaced points; and means responsive to the measured electrical resistance being less than a predetermined value for applying electrical voltage across said electrodes to activate said electrically resistive heating elements so as to heat and thereby regenerate the electrical insulating medium between the first and second longitudinally spaced points.

12. A method of measuring fouling of and heating an elongated electrical insulating medium, said method comprising the steps of:

(a) contacting the elongated electrical insulating medium with an elongated electrically resistive heating element having an elongated electrically conductive sheath therearound, with an electrically insulating zone intermediate the ends of the sheath to divide the sheath into first and second electrically resistive heating zones;

(b) contacting first and second longitudinally spaced points on the sheath in the first and second electrically resistive heating zones, respectively, with first and second electrodes;

(c) measuring the electrical resistance between the first and second electrodes to obtain an indication of fouling of the electrical insulating medium between the first and second longitudinally spaced points; and (d) when the measured resistance between the first and second electrodes indicates that the electrical insulating medium is fouled to a preselected amount, applying electrical voltage across the electrodes to activate the electrically resistive heating elements so as to heat and thereby regenerate the electrical insulating medium between the first and second longitudinally spaced points.

13. A device as claimed in claim 8, further comprising third and fourth electrically resistive heating elements formed as conductive loops adapted to be wrapped around the electrical insulating medium at positions spaced from said first and second heating elements so as to have a second portion of the electrical insulating medium providing a second insulating zone in a second gap between the third and fourth heating elements; and third and fourth electrodes contacting said third and fourth heating elements, respectively, on either side of the second insulating zone.

14. A device as claimed in claim 13, further comprising means for applying power from an electrical power supply to said electrodes in response to measurement of an electrical resistance value indicating fouling of the insulating medium.

15. A device as claimed in claim 14, wherein said means comprises an electronic computer.

16. A device for measuring fouling of and for locally heating an electrical insulating medium, said device comprising:

a first electrically resistive, loop-shaped heating element having a first electrically conductive sheath therearound, with a first insulating zone intermediate the ends of said first electrically conductive sheath, said first loop-shaped heating element adapted to be wrapped around the electrical insulating medium with said first sheath contacting the electrical insulating medium;

a second electrically resistive, loop-shaped heating element having a second electrically conductive sheath therearound, with a second insulating zone intermediate the ends of said second electrically conductive sheath, said second loop-shaped heating element adapted to be wrapped around the electrical insulating medium at a location longitudinally spaced from said first heating element, with said second sheath contacting the electrical insulating medium; and a plurality of spaced apart electrodes contacting said first and second conductive sheaths on either side of said first and second insulating zones.

* * * * *